United States Patent [19]

Lacroix et al.

[11] Patent Number: 5,164,481

[45] Date of Patent: Nov. 17, 1992

[54] PEPTIDES AND ANALOGUES AND MIXTURES THEREOF FOR DETECTING AND ELICITING ANTIBODIES TO RUBELLA VIRUS

[75] Inventors: Martial Lacroix, Brossard; Maan Zrein, Laval; Gervais Dionne, Ville St-Laurent, all of Canada

[73] Assignee: IAF Biochem International Inc., Laval, Canada

[21] Appl. No.: 397,767

[22] Filed: Aug. 23, 1989

[51] Int. Cl.$^5$ .................... C07K 7/00; A61K 37/00; A61K 37/02

[52] U.S. Cl. ................................. 530/324; 530/329

[58] Field of Search ............................... 530/324-329

[56] References Cited

FOREIGN PATENT DOCUMENTS 0299673  7/1988  European Pat. Off. .
2206587.  7/1988  United Kingdom .

OTHER PUBLICATIONS

Frey et al, (1986) *Virology*, 154, 228-232.
Lozzi, et al. (1990) *Arch. Virol.*, 110, 271-276.
Sutcliffe et al. (1983) *Suime*, 219, 660-666.
Hopp et al. (1981) *Proc. Natl. Acad. Sci. USA*, 78, 3824-3828.
Niman et al. (1983) *Proc Natl. Acad. Sci., USA*, 80, 4949-4953.
Terry et al. (1988) *Arch. Virol.*, 98,. 189-197.
P. Argos, "A Possible Homology Between Immunodeficiency . . . Prediction Of HIV p24 Antigenic Sites", *EMBO Journal*, 8(3), pp. 779-785 (1989).
S. Avrameas, "Coupling of Enzymes To Proteins With Glutaraldehyde", *Immunochemistry*, 6, 43-52 (1969).
A. Chagnon and P. Laflamme, "Effect Of Acidity On Rubella Virus", *Canadian Journal of Microbiology*, 10, pp. 501-503 (1964).
D. M. Clarke et al., "Nucleotide Sequence and In Vitro . . . Encoding the Structural Proteins $E_1$, $E_2$ and C", *Nucleic Acids Research*, 15(7), pp. 3041-3057 (1987).
T. K. Frey et al., "Molecular Cloning And Sequencing Of The Region Of The Rubella Virus Genome Coding For Glycoprotein E1", *Virology*, 154, pp. 228-232 (1986).
K. Herrmann, "Rubella Virus", *Diagnostic Procedures For Viral, Rickettsial And Chlamydial Infections*, Lennette and Schmidt (eds.) 5th Edition, American Public Health Association Inc., Washington, pp., 725-766 (1979).
L. Ho-Terry et al., "Analysis Of Rubella Virus Complement-Fixing Antigens By Polyacrylamide Gel Electrophoresis", *Archives of Virology*, 87, pp. 219-228 (1986).
L. Ho-Terry et al., "Immunological Characterisation of the Rubella El Glycoprotein", *Archives of Virology*, 90, pp. 145-152 (1986).
R. Maiolini et al., "A Sandwich Method of Enzyme-Immunoassay, II. Quantification of Rheumatoid Factor", *Journal of Immunological Methods*, 20, pp. 25-34 (1978).
J. Meienhofer et al., "Solid Phase Synthesis Without Repetitive Acidolysis", *Int. J. Peptide Protein Res.*, 13, pp. 35-42 (1979).
S. V. Nates et al., "Comparison of Immune Response to Rubella Virus Proteins in Early and Late Natural Infections", *Microbiologica*, 12, pp. 335-338 (1989).
P. D. Parkman et al., "Attenuated Rubella Virus", *The New England Journal of Medicine*, 275(11), pp. 569-574 (1966).

(List continued on next page.)

*Primary Examiner*—David M. Naff
*Assistant Examiner*—Jon P. Weber
*Attorney, Agent, or Firm*—James F. Haley, Jr.; Leslie A. McDonell

[57] ABSTRACT

Linear and cyclic peptides of the E1 and C protein of the rubella virus are disclosed. These peptides and analogues, mixtures and combinations of them are useful in detecting and quantifying antibodies raised against the rubella virus. They are also useful in raising antibodies to the rubella virus for use in the diagnosis of and protection against rubella viral infections.

2 Claims, 2 Drawing Sheets

OTHER PUBLICATIONS

J. W. Partridge et al., "Congenital Rubella Affecting an . . . Before Conception", *British Medical Journal*, 282, pp. 187–188 (1981).

J. Peetermans and C. Huygelen, "The Use of Pigeon Red Blood Cells in the Rubella Virus Hemagglutination–Inhibition Test", Presse Med. 75, pp. 2177–2178 (1967).

L. E. Schaefer et al., "Evaluation of Microparticle Enzyme . . . and *Toxoplasma-gondii* On the Abbott IMx Automated Analyzer", 27(11), pp. 2410–2413 (1989).

C. Stahli et al., "High Frequencies of Antigen-Specific Hybridomas: . . . Prediction by Spleen Cell Analysis", *Journal of Immunological Methods*, 32, pp. 297–304 (1980).

R. S. Steece et al., "Comparison of Enzyme-Linked . . . Rubella Immune Status", *Journal of Clinical Microbiology*, 21(1), pp. 140–142 (1985).

Takkinen et al., "Nucleotide Sequence of the Rubella Virus Capsid Protein Gene Reveals an Unusually High G/C Content", *Journal of General Virology*, 69, pp. 603–612 (1988).

G. M. Terry et al., "Localization of the Rubella E1 Epitopes", *Archives of Virology*, 98, pp. 189–197 (1988).

G. M. Terry et al., "A Bio-Engineered Rubella E1 Antigen", *Archives of Virology*, 104, pp. 63–75 (1989).

M. Trudel et al., "Identification of Rubella Virus Structural Proteins by Immunoprecipitation", *Journal of Virological Methods*, 5, pp. 191–197 (1982).

A. Voller and D. E. Bidwell, "A Simple Method for Detecting Antibodies to Rubella", *British Journal of Experimental Pathology*, 56, pp. 338–339 (1975).

Z. Wang and S. Han, "Tryptic Peptide Map Analysis of . . . Strains", *Shandong Yike Daxue Xuebao*, 24(3), pp. 6–10 (abstract p. 15) (1986).

FIGURE 1

AMINO ACID SEQUENCE OF THE RUBELLA E1 GLYCOPROTEIN
(JUDITH STRAIN)

EEAFTYLC

FIGURE 2

```
      1         10
      MASTTPITME  DLQKALEAQS  RALRAELAAG  ASQSRRPRPP  RQRDSSTSGD
                  20
BCH-229 ─────────────┘
      DSGRDSGGPR  RRRGNRGRGQ  RRDWSRAPPP  PEERQESRSQ  TPAPKPSRAP
      PQQPQPPRMQ  TGRGGSAPRP  ELGPPTNPFQ  AAVARGLRPP  LHDPDTEAPT
      EACVTSWLWS  EGQGAVFYRV  DLHFTNLGTP  PLDEDGRWDP  ALMYNPCGPE
      PPAHVVRAYN  QPAGDVRGVW  GKGERTYAEQ  DFRVGGTRWH  RLLRMPVRGL
      DGDSAPLPPH  TTERIETRSA  RHPWRIR
```

PEPTIDES AND ANALOGUES AND MIXTURES THEREOF FOR DETECTING AND ELICITING ANTIBODIES TO RUBELLA VIRUS

TECHNICAL FIELD OF THE INVENTION

This invention relates to novel linear and cyclic peptides and mixtures and combinations thereof useful for detecting and quantifying rubella infections and for eliciting antibodies specific to the rubella virus. These peptides are also useful in vaccines against rubella viral infections.

BACKGROUND OF THE INVENTION

Rubella was first described in Germany in the 18th century and is, therefore, often referred to as German measles. It is a highly contagious disease characterized by a general rash and a mild fever. Its clinical aspects were, for a long time, confused with other infections, including measles. The major risk associated with rubella infection occurs during pregnancy when severe damage to the fetus can result in deafness, cataracts, cardiac abnormalities and microencephaly.

The rubella virus, the etiologic agent of rubella, belongs to the Togaviridae family. It is a roughly spherical enveloped virus about 60 nm in diameter. Its genome consists of a single positive stranded RNA (10 Kb). The envelope contains lipoproteins derived from host infected cells, a non-glycosylated nucleocapsid protein—C(33K)—and two glycoproteins—E1(58K) and E2(42-47K). The latter, responsible for the hemagglutination activity of the rubella virus, are acylated and linked by disulfide bonds.

Three strains of rubella virus (Therien, Judith, M33) have been described and portions of their genomes have been sequenced (Frey et al., 1986, Virology 154, 228-232; Terry et al., 1988, Arch. Virol. 98, 189-197; Clarke et al., 1987, Nucl. Acids Res. 15, 3041-3057).

Although rubella can be diagnosed by inoculating infected materials (usually nasopharyngeal secretions) into susceptible cell cultures, the most widely used diagnostic tests are based on the hemagglutinating properties of its glycoproteins. In those assays ("HAI"), the presence in a serum sample of antibodies to a hemagglutinin prevents the virus from binding to red blood cells (usually from chicken blood) thus inhibiting hemagglutination (Peetermans and Huygelen, 1967, Presse Med. 75, 2177-2178 and Lennette and Schmidt, 1979, in "*Diagnostic procedures for viral, rickettsial and chlamydial infections*", 5th Ed., American Public Health Association Inc., Washington). In such assays an increase in HAI antibody titers reflects a recent infection.

Since the introduction of enzyme-labeled antibodies (Avrameas, 1969, Immunochemistry 6, 43-52), enzyme-linked-immunosorbent (ELISA) have been used for the diagnosis of a large variety of viral and bacterial infections, including rubella infections. Serodiagnosis of rubella infections using ELISA techniques, for example, was first described by Voller and Bidwell (1975, Br. J. Exp. Pathol. 56, 338-339).

In ELISA, viral extracts are typically coated onto the surface of plastic wells and antibodies (if any) in a serum sample or analyte are bound to the adsorbed proteins from the viral extracts. After appropriate washing, the presence of antibodies bound to the proteins in the well is detected using antibodies to human immunoglobulins conjugated to a signal, such as a horseradish peroxidase. After washing off unbound signal, the levels of enzymatic activity in each well are measured. Other forms and variations of ELISA are also well known and often used.

The introduction of ELISA for the specific determination of rubella IgM and IgG has been responsible for the rapid decline (i.e., from 45% in 1978-1980 to 19% in 1982) of HAI diagnostic assays for rubella viral infections (Steece et al., 1985, J. Clin. Microbiol. 21 (1), 140-142). Compared to HAI tests, ELISA requires no pretreatment of the sera and only one or two dilutions per serum sample. The amount of antigenic material used in ELISA is also smaller than what was required in the former HAI assays.

There are unfortunately several problems with presently used ELISA diagnostic tests for rubella infection. Specifically, internal variations between wells and between different batches of rubella antigens used to coat the wells are often observed. These variations are likely a consequence of various difficulties encountered in reproducibly isolating the rubella virus from host cell cultures.

The production of the rubella virus in tissue cultures is technically difficult. The virus grows to low titers, is difficult to separate from cellular membrane debris and is highly labile (Ho-Terry et al. 1986, Arch Virol. 87, 219-228; Chagnon and LaFlamme, 1964, Can. J. Microbiol. 10, 501-03). This makes it difficult to isolate the virus from cellular debris originating from host cells. In an attempt to overcome this problem, most ELISA techniques for detecting rubella infection employ a series of wells coated with extracts prepared with uninfected cells and another series of wells coated with extracts prepared from rubella-infected cells. Each serum sample is then tested on both series of wells and the net response is calculated by subtraction of the signal measured on the wells coated with extracts prepared with uninfected cells from the one measured on the wells coated with extracts prepared with rubella-infected cells.

Terry et al. (1988, Arch. Virol. 98, 189-197) and Ho-Terry et al. (1986, Arch. Virol. 90, 145-152 and European Patent Application No. 88306191.3) refer to the reactivity of three non-competing monoclonal antibodies directed against the rubella E1 glycoprotein. The epitopes bound by each of these monoclonal antibodies have been identified and are designated EP1, EP2 and EP3. Monoclonal antibodies directed to EP1 and EP2 exhibit both hemagglutination inhibition and neutralizing activity. Monoclonal antibodies to EP3 exhibit only neutralizing activity. The exact location of these three epitopes in the viral genome is shown in FIG. 1. None of these documents describes synthetic peptides corresponding to the EP1, EP2 or EP3 epitopes. It is thus not known how useful synthetic peptides corresponding to such epitopes might be in the development of a diagnostic test for rubella antibody detection.

The rubella pandemic of 1963-1965 prompted the development of a vaccine against rubella. (Parkman et al., 1966, N. Engl. J. Med. 275, 569-574). It was comprised of live attenuated viruses and is immunogenic in at least 95% of the recipients. While neutralizing antibodies appear later than following a natural infection and at levels as much as ten-fold lower, the vaccine-stimulated antibodies nonetheless effectively protect recipients from the disease. The present rubella vaccines, however, have some drawbacks. For example, a significant proportion of vaccinees suffer occasional arthritis (mainly seen in adult women), mild rash, fever and lymphadenopathy. Protection conferred by the vaccine also lasts for only 5-10 years, rather than the longer-lasting immunity that follows natural infection. Most importantly, small amounts of infectious virus typically appear in the nasopharynx 2-3 weeks after immunization, making vaccination very dangerous for pregnant women coming in close contact with a recently vaccinated person or even worse having herself been vaccinated while not knowing she was pregnant.

Vaccines based on synthetic or recombinant peptides would not present this hazard because the antigenic material would be totally innocuous. However, such vaccines are not now available and the immunogenicity and neutralizing properties of peptide-based vaccines are unknown. Furthermore, not all peptides are expected to be useful in vaccines. For example, high antibody titers in HAI tests do not correlate well with protection against rubella infection (Partridge et al., 1981, Br. Med. J. 282, 187-188). This may be due to the fact that epitopes involved in hemagglutination and neutralization are different (Trudel et al, 1982, J. Virol. Methods 5, 191-197). Diagnosis based on the detection of neutralizing antibodies, on the other hand, should have a high predictive value for immune status and prevention of rubella infection.

These differences are important, not only in evaluating peptide-based vaccines against rubella but in assaying the immune status of patients with respect to rubella infectivity. For example, the "purified" rubella antigens now available are potentially infective and carry both the hemagglutinating and neutralizing epitopes. Thus, specific tests for immune status using these antigens are questionable, and the antigens used in those vaccines may be infectious.

Considering these problems, we have selected certain peptide sequences on the E1 and C proteins of the rubella virus and prepared peptides defined by them. Our peptides selected for their ability to bind high levels of antibodies, as measured by an ELISA, are useful in diagnostic tests for rubella infection. Peptides of this invention recognized by neutralizing antibodies are also useful as the active ingredient of a totally innocuous rubella vaccine.

SUMMARY OF THE INVENTION

Novel peptides are disclosed for use in the screening of blood or body fluids for prior exposure to the rubella virus and in the preparation of a safe, effective vaccine against rubella infections. Peptides incorporating a cyclic structure preferably formed by the joining of two cysteine residues in those peptides are surprisingly more active, both in diagnosis, and in stimulating protective antibodies, than their linear counterparts and thus are the preferred antigens of this invention.

The peptides of this invention are useful in a wide variety of specific binding assays for the detection of antibodies to rubella virus, as immunogens for eliciting antibodies useful for the detection of rubella antigens or in the preparation of vaccines against rubella viral infections.

BRIEF DESCRIPTION OF THE DRAWINGS

FIG. 1 depicts the amino acid sequence of the E1 glycoprotein of the rubella virus (Judith strain). The amino acids of the sequence are given using the following single letter code: A=ala, C=cys, D=asp, E=glu, F=phe, G=gly, H=his, I=ile, K=lys, L=leu, M=met, N=asn, P=pro, Q=gln, R=arg, S=ser, T=thr, V=val, W=trp, Y=tyr.

The glycosylation sites are indicated as either putative (?) or confirmed (■). The designations -- EP1, EP2 and EP3 -- denote the three epitopes identified by Terry et al. and Ho-Terry et al., supra. The designations -- BCH-139, BCH-139 cyclic, BCH-140, BCH-140 cyclic, BCH-174, BCH-176, BCH-177, BCH-178 and BCH-178 cyclic -- denote various peptides of this invention. The double line displays the cyclic structure of certain of the recited polypeptides.

FIG. 2 depicts the amino acid sequence of the C protein of the rubella virus (Therien strain). The designation -- BCH-229 -- denotes a particular peptide of this invention.

DESCRIPTION OF THE INVENTION

The present invention provides novel peptides corresponding to regions of the E1 glycoprotein and C protein of the rubella virus. It also provides analogues of those peptides and mixtures and combinations of those peptides and analogues. As will be plain from the following description, these peptides, analogues, mixtures and combinations are useful in a wide variety of diagnostic and preventive methods, means and compositions with respect to the rubella virus and infections caused by it.

The peptides of this invention are selected from the group consisting of:

(i) peptides having the formula:

$$a-X-b$$

wherein:

X is a sequence of at least six amino acids taken as a block from the amino acid sequence of the E1 glycoprotein of a strain of rubella virus that corresponds to $AA_{213}-AA_{291}$ of the E1 glycoprotein of the Judith strain of rubella virus, analogues thereof and inverts of that block and those analogues;

a is an amino terminus, one to eight amino acids or a substituent effective to facilitate coupling or to improve the immunogenic or antigenic activity of the peptide; and b is a carboxy terminus, one to eight amino acids or a substituent effective to facilitate coupling or to improve the immunogenic or antigenic activity of the peptide; and (ii) peptides having the formula:

$$a-Z-b$$

wherein:

Z is a sequence of at least six amino acids taken as a block from the amino acid sequence of the C protein of a strain of rubella virus that corresponds to $AA_1-AA_{21}$ of the C protein of the Therien strain of rubella virus, analogues thereof and inverts of that block and those inserts and a and b are as defined above.

In this description, the amino acid sequence and numbering published by Terry et al. (Arch. Virol. 98, 189-197, 1988) for the E1 glycoprotein of the Judith strain and by Takkinen et al. (J. Gen. Virol. 69, 603-612, 1988) for the C protein of the Therien strain are used (for ease of reference only) to designate and to depict the particular amino acid sequences of the peptides of this invention. However, these peptides, and their analogues, and their inverts are useful in the diagnosis and prevention of all strains of the Rubella virus, including, for example, strains Therien, Judith and M33. Moreover, peptides characterized by amino acid sequences of the corresponding regions of the E1 glycoprotein and C protein of those strains and their analogous are also included within the scope of this invention and the claims of this application. And the terms "corresponds" and "corresponding" are meant to refer to the native amino acids of those defined regions in any strains of rubella virus.

This invention also includes analogues of the peptides described above. As used herein "analogues" denote amino acid insertions, deletions, substitutions and modifications at one or more sites in the peptide chain in that portion of it that consists of the block of the naturally occurring rubella amino acid sequences. However, as described above, irrespective of such insertions, deletions, substitutions and modifications, the peptides of this invention must contain at least six amino acids taken as a block from, for example, $AA_{213}$-$AA_{291}$ of the E1 glycoprotein of the Judith strain of the rubella virus or an invert of that block or at least six amino acids taken as a block from, for example, $AA_1$ to $AA_{21}$ of the C protein of the Therien strain of the rubella virus or an invert of that block.

Preferred modifications and substitutions to the native amino sequence block in the peptide chain are conservative ones (i.e., those having minimal influence on the secondary structure and hydropathic nature of the peptide). These include substitutions such as those described by Dayhoff in the Atlas of Protein Sequence and Structure 5, 1978 and by Argos in EMBO J. 8, 779-785, 1989. For example, amino acids belonging to one of the following groups represent conservative changes: ala, pro, gly, glu, asp, gln, asn, ser, thr; cys, ser, tyr, thr; val, ile, leu, met, ala, phe; lys, arg, his; and phe, tyr, trp, his. In like manner, methionine, an amino acid which is prone to oxidation may be replaced by norleucine. They also include substitutions of D isomers for the corresponding L amino acids.

The term "amino acid" as employed in this description (e.g., in the definition of a and b) except when referring to the amino acids taken as a block from the E1 glycoprotein or C protein of the rubella virus, encompasses all of the natural amino acids, those amino acids in their D-configurations, and the known non-native, synthetic, and modified amino acids, such as homocysteine, ornithine, norleucine and β-valine.

The terms "inverted sequences" or "inverts" employed in this description mean an amino acid sequence in reverse order to a designated amino acid sequence. For example, ARQTP is the invert of amino acid sequence PTQRA.

Figure 1:
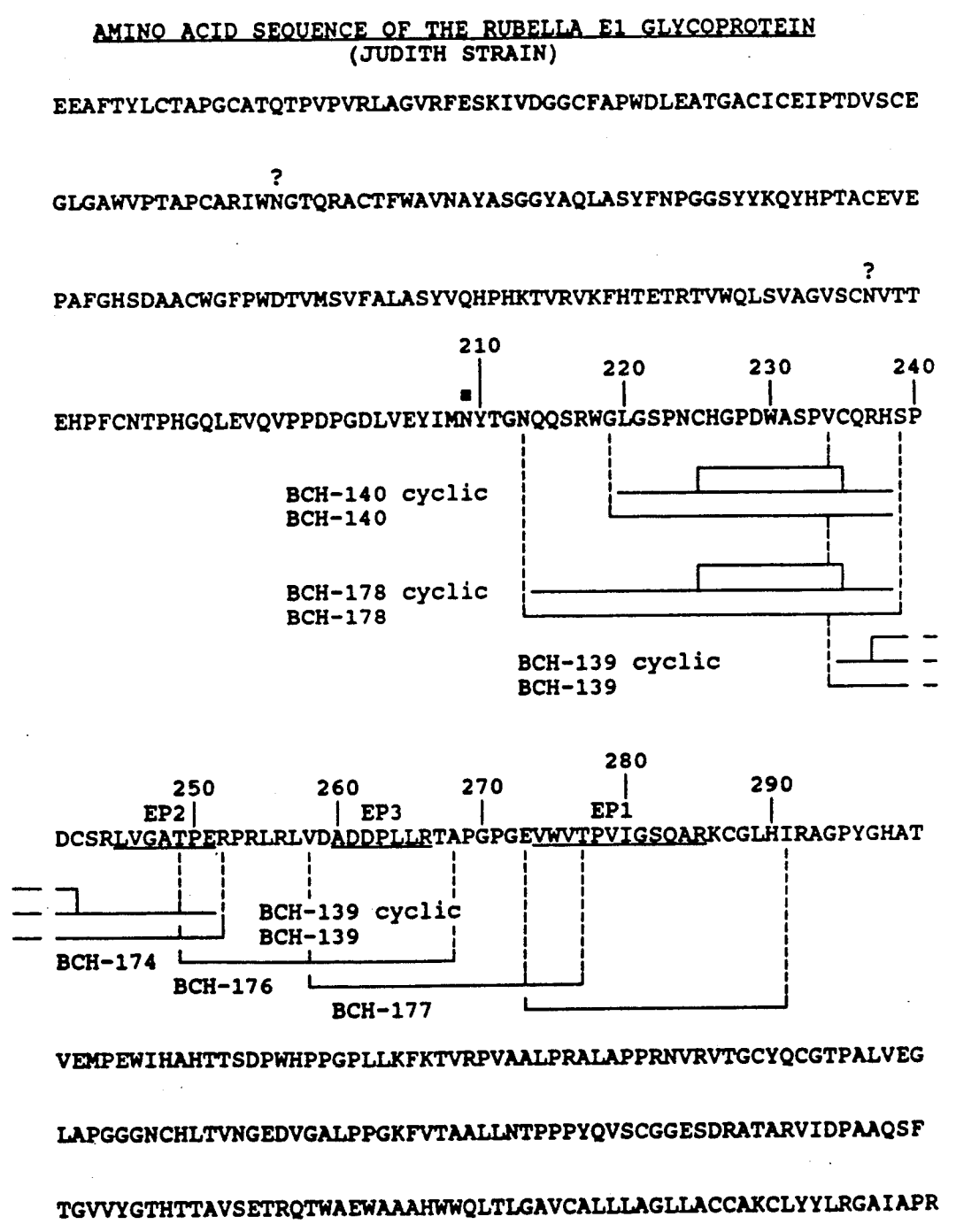

Illustrative of the peptides of this invention are peptides within the above formulae wherein X is an amino acid sequence of the E1 glycoprotein of a strain of rubella virus that corresponds to a sequence selected from the group consisting of $AA_{213}$-$AA_{239}$, $A_{219}$-$AA_{239}$, $AA_{234}$-$AA_{252}$, $AA_{249}$-$AA_{268}$, $AA_{258}$-$AA_{277}$ and $AA_{273}$-$AA_{291}$ of the E1 glycoprotein of the Judith strain, and analogues thereof, and inverts of those sequences and analogues, and wherein Z is an amino acid sequence of the C protein of a strain of rubella virus that corresponds to the sequence $AA_1$-$AA_{21}$ of the C protein of the Therien strain, analogues thereof and inverts of that sequence and those analogues. See, e.g., FIGS. 1 and 2.

The peptides of this invention as defined in these formulae may be linear or cyclic. We, however, prefer cyclic peptides for both diagnostic uses and as the active components of the vaccines of this invention.

Illustrative of the linear peptides of this invention are the following E1 glycoprotein derived peptides (using amino acid sequences of the Judith strain for case of references):
BCH-139: a-VCQRHSPDCSRLVGATPER-b
BCH-140: a-GLGSPNCHGPDWASPVCQRHS-b
BCH-174: a-TPERPRLRLVDADDPLLRTA-b
BCH-176: a-VDADDPLLRTAPGPGEVWVT-b
BCH-177: a-EVWVTPVIGSQARKCGLHI-b
BCH-178: a-NQQSRWGLGSPNCHGPDWASPVCQRHS-b
and the following C protein derived peptide (using the Therien strain for ease of reference):
BCH-229: a-MASTTPITMEDLQKALEAQSR-b
wherein a and b are as defined above as well as analogues thereof. BCH-140 and BCH-178 are preferred and BCH-178 is most preferred.

Preferred cyclic peptides of this invention have the following formulae (using the amino acid sequence and numbering of the E1 glycoprotein of the Judith strain for ease of reference):

(i) a-B—CHGPDWASPVC—J-b
       └─────────────┘ wherein:
B, if present, is one to twelve amino acids corresponding to amino acid $AA_{224}$ to $AA_{213}$-$AA_{224}$ of the E1 glycoprotein of the Judith strain of rubella virus and analogues thereof;
J, if present, is one to seventeen amino acids corresponding to $AA_{236}$ to $AA_{236}$-$AA_{252}$ of the rubella E1 glycoprotein of the Judith strain of rubella virus and analogues thereof; and
a and b are as defined above; and (ii) a-O—CQRHSPDC—U-b
       └──────────┘ wherein:
O, if present, is one to twenty-two amino acids corresponding to $AA_{234}$ to $AA_{213}$-$AA_{24}$ of the E1 glycoprotein of the Judith strain of rubella virus and analogues thereof;
U, if present, is one to ten amino acids corresponding to $AA_{243}$ to $AA_{243}$-$AA_{252}$ of the E1 glycoprotein of the Judith strain of rubella virus and analogues thereof; and
a and b are as defined above; and
(iii) inverts of those amino acid sequences.

More preferred cyclic peptides of this invention (using the E1 glycoprotein of the Judith strain for ease of references) are:

BCH-139 cyclic: a-VCQRHSPDCSRLVGATPER-b
                  └─────────┘

BCH-140 cyclic: a-GLGSPNCHGPDWASPVCQRHS-b
                      └───────────────┘

BCH-178 cyclic: a-NQQSRWGLGSPNCHGPDWASPVCQRHS-b
                            └───────────────┘ wherein a and b are as defined above as well as analogues thereof. The most preferred cyclic peptide of this invention (using the E1 glycoprotein of the Judith strain for ease of reference) is:

BCH-178 cyclic: a-NQQSRWGLGSPNCHGPDWASPVCQRHS-b
(with a bracket connecting the two cysteines)

wherein a and b are as defined above and analogues thereof.

Also within the scope of the present invention are combinations or mixtures of the cyclic and linear synthetic peptides of this invention. For example, a preferred peptide mixture for the detection of antibodies specific to the rubella virus comprises synthetic peptide BCH-178 cyclic or analogues thereof and any other cyclic or linear peptide of this invention. A more preferred peptide mixture for the detection of antibodies specific to the rubella virus comprises synthetic peptides BCH-178 cyclic and BCH-229 or analogues thereof.

It may also be desirable to covalently join two or more peptide sequences of this invention or even to form a polymer consisting of two or more peptides of this invention. Such changes may facilitate passive adsorption of the peptides to a solid surface without loss of their antigenic properties. It may also be desirable to covalently join one or more synthetic peptides of this invention with a synthetic peptide known to carry a T-cell epitope, the resulting conjugate being more useful as an immunogen.

One surprising feature of the preferred and most preferred peptides of this invention is that peptides spanning a region outside of the previously identified epitopes EP1, EP2 and EP3 are more sensitive in the detection of rubella-specific antibodies than peptides including one or more of those epitopes. For example, BCH-140 and BCH-178, which do not include any of the previously identified epitopes, show improved diagnostic characteristics as compared to BCH-139, BCH-174, BCH-176 and BCH-177, which include one or more of the previously identified epitopes.

Another surprising feature of the preferred and most preferred peptides of this invention is that cyclization augments their antigenicity. For example, ELISA assays using plates coated with BCH-139 cyclic, BCH-140 cyclic and BCH-178 cyclic all showed a higher sensitivity for the detection of rubella-specific antibodies than plates sensitized with their linear counterparts (Table 1). Moreover, signals with seronegative samples were also often reduced with the cyclic peptides. Table 1 also illustrates the superiority of peptide BCH-178 cyclic over peptide BCH-140 cyclic and peptide BCH-139 cyclic.

Another unexpected advantage of the novel peptides of this invention is that they are capable of providing complete detection of rubella-specific antibodies derived from a panel of 109 samples with known HAI titers. Peptide BCH-178 cyclic is the most preferred example of peptides having this advantage. Another advantage of the peptides of this invention is the high level of specificity displayed by them. This results in a minimal number of false positives.

As described above by a and b, it is often useful and certainly within the scope of this invention to modify the peptide block consisting of the naturally occurring rubella amino acid sequences in the peptides of this invention in order to make the chosen peptide more useful as an immunodiagnostic reagent or as an active ingredient of a vaccine. Such changes, for example, include:

addition of a cysteine residue to one or both terminals in order to facilitate coupling of the peptide to a suitable carrier with heterobifunctional cross-linking reagents such as sulfosuccinimidyl-4-(p-maleimidophenyl) butyrate, a preferred reagent for effecting such linkages, sulfosuccinimidyl-4-(N-maleimidomethyl)cyclohexane-1-carboxylate and N-succinimidyl-3-(2-pyridyldithio) propionate;

addition of 1 to 8 additional amino acids at one or both terminals of the peptide to facilitate linking of the peptides to each other, for coupling to a support or larger peptide or protein or for modifying the physical or chemical properties of the peptide. Examples of such changes may be effected by addition of tyrosine, glutamic acid or aspartic acid which can be used as linkers via an esterification reaction and lysine which can be linked via Schiff base or amide formation. As described above such additional amino acids include all of the natural amino acids, those amino acids in their D-configurations, and the known non-native, synthetic and modified amino acids; and derivatization of one or both terminals of the peptide by, for example, acylation or amidation. These modifications result in changes in the net charge on the peptide and can also facilitate covalent linking of the peptide to a solid support, a carrier or another peptide. Examples of the substituents effective to facilitate coupling or to improve the immunogenicity or antigenic activity of the peptide are $C_2$-$C_{16}$ acyl groups, polyethylene glycol and phospholipids.

To prepare the novel peptides of this invention any of the conventional peptide production methodologies may be used. These include synthesis, recombinant DNA technology and combinations thereof. We prefer solid phase synthesis. In that synthetic approach, the resin support maybe any suitable resin conventionally employed in the art for the solid phase preparation of peptides. Preferably, it is a p-benzyloxyalcohol polystyrene or p-methylbenzydrylamine resin. Following the coupling of the first protected amino acid to the resin support, the amino protecting group is removed by standard methods conventionally employed in the art. After removal of the amino protecting group, the remaining α-amino protected and, if necessary, side chain protected amino acids are coupled, sequentially, in the desired order to obtain the chosen peptide. Alternatively, multiple amino acid groups may be coupled using solution methodology prior to coupling with the resin-supported amino acid sequence.

The selection of an appropriate coupling reagent follows established art. For instance, suitable coupling reagents are N,N'-diisopropylcarbodiimide or N,N'-dicyclohexylcarbodiimide (DCC) or benzotriazol-1-yloxy-tris(dimethylamino)phosphonium hexafluorophosphate either alone or preferably in the presence of 1-hydroxybenzotriazole. Another useful coupling procedure employs preformed symmetrical anhydrides of protected amino acids.

The necessary α-amino protecting group employed for each amino acid introduced onto the growing polypeptide chain is preferably 9-fluorenylmethyloxycarbonyl (FMOC), although any other suitable protecting group may be employed as long as it does not degrade under the coupling conditions and is readily removable selectively in the presence of any other protecting group already present in the growing peptide chain.

The criteria for selecting protecting groups for the side chain amino acids are: (a) stability of the protecting group to the various reagents under reaction conditions selective for the removal of the α-amino protecting group at each step of the synthesis; (b) retention of the protecting group's strategic properties (i.e., not be split off under coupling conditions) and (c) removability of protecting group easily upon conclusion of the peptide synthesis and under conditions that do not otherwise affect the peptide structure.

The fully protected resin-supported peptides are preferably cleaved from the p-benzyloxy alcohol resin with 50% to 60% solution of trifluoroacetic acid in methylene chloride for 1 to 6 hours at room temperature in the presence of appropriate scavengers such as anisole, thioanisole, ethyl methyl sulfide, 1,2-ethanedithiol and related reagents. Simultaneously, most acid labile side-chain protecting groups are removed. More acid resistant protecting groups are typically removed by HF treatment.

The preferred cyclic peptides of the invention may be prepared from the linear peptides of this invention by any of the well-known synthetic cyclization methodologies. Preferably, two existing thiol containing residues, such as cysteine, are employed. However, a thiol residue may, instead, be substituted for a non-thiol residue to effect cyclization. For example, the cyclic synthetic peptides of this invention may be prepared by the direct oxidative conversion of protected or unprotected SH-groups to a disulfide bond by techniques generally known in the art of peptide synthesis. The preferred method involves the direct oxidation of free SH-groups with potassium ferricyanide. Alternatively, cyclization may be effected using substituents a and b.

The peptides of the present invention are useful as diagnostic reagents for the detection and quantification of rubella virus-associated antibodies in accordance with methods well-known in the art. These include ELISA, hemagglutination, single-dot and multi-dot methods and assays.

A preferred convenient and classical technique for the determination of antibodies against the rubella virus using a peptide or a peptide mixture or combination of this invention is an enzyme-linked immunosorbent assay (ELISA). In this assay, for example, a peptide or a peptide mixture or combination of this invention is adsorbed onto, or covalently coupled to, the wells of a microtiter plate. The wells are then treated with the sera or analyte to be tested. After washing, anti-human IgG or anti-human IgM labeled with peroxidase is added to the wells. The determination of the peroxidase is performed with a corresponding substrate, e.g., 3,3',5,5'-tetramethylbenzidine. Without departing from the usefulness of this illustrative assay, the peroxidase can be exchanged by another label, e.g., by a radioactive, fluorescence, chemiluminescence or infra-red emitting label.

Another method for the determination of antibodies against rubella virus with the peptides of this invention is an enzyme immunological test according to the so-called "Double-Antigen-Sandwich-Assay". This method is based on the work of Maiolini, as described in Immunological Methods, 20, 25–34, 1978. According to this method, the serum or other analyte to be tested is contacted with a solid phase on which a peptide of this invention has been coated (capture layer) and with a peptide of this invention which has been labeled with peroxidase or other label (probe layer). The immunological reaction can be performed in one or two steps. If the immunological reaction is performed in two steps, then a washing step is typically carried out between the two incubations. After the immunological reaction or reactions, a washing step is performed. Thereafter, the peroxidase or other signal is determined, e.g., using o-phenylene diamine for peroxidase. Other enzymes and chromogens, including those already described, can also be employed in this assay.

Suitable solid phases for use in the above-described assays and assay methods include organic and inorganic polymers, e.g., amylases, dextrans, natural or modified celluloses, polyethylene, polystyrene, polyacrylamides, agaroses, magnetite, porous glass powder, polyvinyldiene fluoride (kynar) and latex, the inner wall of test vessels (i.e., test tubes, titer plates or cuvettes of glass or artificial material) as well as the surface of solid bodies (i.e., rods of glass and artificial material, rods with terminal thickening, rods with terminal lobes or lamallae). Spheres of glass and artificial material are especially suitable as solid phase carriers.

The peptides of this invention and the mixtures and combinations of them are not only useful in the determination and quantification of antibodies against rubella virus. They are also useful for the determination and quantification of rubella virus antigens themselves because these peptides either free, polymerized or conjugated to an appropriate carrier are useful in eliciting antibodies, in particular and preferably monoclonal antibodies, immunologically cross reactive to the antigens of the rubella virus. Such antibodies, for example, can be produced by injecting a mammalian or avian animal with a sufficient amount of the peptide to elicit the desired immune response and recovering said antibodies from the serum of said animals. Suitable host animals for eliciting antibodies include, for example, rabbits, horses, goats, guineapigs, rats, mice, cows, sheep and hens. Preferably, hybridomas producing the desired monoclonal antibodies are prepared using the peptides of this invention and conventional techniques. For example, the well-known Kohler and Milstein technique for producing monoclonal antibodies may be used. In order to distinguish monoclonal antibodies which are directed against the same antigen, but against different epitopes, the method of Stähli et al. (J. of Immunological Methods, 32, 297–304, 1980) can be used.

Various methods which are generally known can be employed in the determination or quantification of the rubella virus or a portion thereof using the above antibodies. In one such procedure, known amounts of a serum sample or other analyte to be assayed, a radiolabeled linear or cyclic peptide of this invention or a mixture or combination of those peptides and an unlabeled peptide of this invention or a mixture or combination thereof, are mixed together, a given amount of an antipeptide, preferably a monoclonal antibody, is added and the mixture allowed to stand. The resulting antibody/antigen complex is then separated from the unbound reagents by procedures known in the art, i.e., by treatment with ammonium sulphate, polyethylene glycol, a second antibody either in excess or bound to an insoluble support, or dextran-coated charcoal. The concentration of the labeled peptide is then determined in either the bound or unbound phase and the rubella virus antigen content of the sample determined by comparing the level of labeled component to a standard curve in a manner known per se.

Another suitable method for using these antibodies in assays is the "Double-Antibody-Sandwich-Assay". According to this assay, the sample to be tested is treated with two different antibodies, e.g., raised by immunizing different animals, e.g., sheep and rabbits with a peptide of this invention or a mixture or combination thereof. One of the antibodies is labeled and the other is coated on a solid phase. The preferred solid phase is a plastic bead and the preferred label is horse-radish peroxidase.

Typically in the "Double-Antibody-Sandwich-Assay", the sample is incubated with the solid phase antibody and the labeled antibody. However, it is also possible to contact the sample first with the solid phase antibody and, then after an optional washing, to contact the sample with the labeled antibody. Preferably, however, the sample is treated together with the solid phase and the labeled antibody. After the immunological reaction(s), the mixture is washed and the label is determined according to procedures known in the art. In the case where peroxidase is used as the label, the determination maybe performed using a substrate, e.g., with o-phenylene diamine or with tetramethylbenzidine. The amount of the labeled component is proportional to the amount of the antigen(s) present in the analyte or serum sample.

The methods and assays for the determination and quantification of rubella virus antigens or antibodies against that virus, as described above, can be conducted in suitable test kits comprising, in a container, a peptide of this invention, mixtures or combinations thereof, or antibodies against rubella virus elicited by a those peptides or mixtures and combinations thereof.

The peptides of this invention and mixtures and combinations thereof are also useful as the active component of vaccines capable of inducing protective immunity against the rubella virus in hosts susceptible to infection with that virus. Routes of administration, antigen doses, number and frequency of injections will vary rom individual to individual and may parallel those currently being used in providing immunity to other viral infections. For example, the vaccines of this invention are pharmaceutically acceptable compositions containing at least one peptide of this invention, its analogues or mixtures or combinations thereof, in an amount effective in a mammal, including a human, treated with that composition to raise antibodies sufficient to protect the treated mammal from a rubella viral infection for a period of time.

The vaccines are prepared in accordance with known methods. The vaccine compositions of this invention are conveniently and conventionally combined with physiologically acceptable carrier materials, such as pharmaceutical grade saline, tetanus toxoid, and keyhole limpet hemocyanin. The vaccine compositions of this invention may also contain adjuvants or other enhancers of immune response, such as alum preparations, liposomes or immunomodulators. Furthermore, these vaccine compositions may comprise other antigens to provide immunity against other viruses (e.g., mumps and measles) or pathogens in addition to rubella. The amount of these other antigens is again dependent on the mammal to be treated and the course of the disease. However, the antigen should be present in an amount effective to raise antibodies sufficient to protect the treated mammal from that pathogen or virus for a period of time.

General procedures for the synthesis and utilization of the peptides of this invention are provided below.

PROCEDURE 1

Preparation of Resins Carrying the Nα-FMOC Protected Amino Acid Residue

The desired Nα-FMOC protected amino acid residue in a mixture of methylene chloride ($CH_2Cl_2$) and dimethylformamide (DMF) (4:1) was added to a suspension of p-benzyloxy alcohol resin in $CH_2Cl_2$: DMF (4:1) at 0° C. The mixture was stirred manually for a few seconds and then treated with N,N'-dicyclohexyl- carbodiimide (DCC) followed by a catalytic amount of 4-(dimethylamino) pyridine. The mixture was stirred at 0° C. for an additional 30 minutes and then at room temperature overnight. The filtered resin was washed successively with $CH_2Cl_2$, DMF and isopropanol (3 washes each) and finally, with $CH_2Cl_2$. The resin was suspended in $CH_2Cl_2$, chilled in an ice bath and redistilled pyridine was added to the stirred suspension followed by benzoyl chloride. Stirring was continued at 0° C. for 30 minutes and then at room temperature for 60 minutes. After filtration, the resin was washed successively with $CH_2Cl_2$, DMF and isopropanol (3 washes each) and finally with petroleum ether (twice) before being dried under high vacuum to a constant weight. Spectrophotometric determination of substitution according to Meienhofer et al. (Int. J. Peptide Protein Res., 13, 35, 1979) indicates the degree of substitution on the resin.

PROCEDURE 2

Coupling of Subsequent Amino Acids

The resin carrying the Nα-FMOC protected first amino acid residue was placed in a reaction vessel of a Biosearch 9600 Peptide Synthesizer and treated as follows:

1) Washed with DMF (4 times for 20 sec. each)
2) Prewashed with a 30% solution of piperidine in DMF (3 min.)
3) Deprotected with a 30% solution of piperidine in DMF (7 min.)
4) Washed with DMF (8 times for 20 sec. each)
5) Checked for free amino groups—Kaiser Test (must be positive)
6) The peptide resin was then gently shaken for 1 or 2 hrs with 8 equivalents of the desired FMOC-protected amino acid and 1-hydroxybenzotriazole and benzotriazol-1-yloxy-tris(dimethylamino)phosphonium hexafluorophosphate all dissolved in dry redistilled DMF containing 16 equivalents of 4-methylmorpholine.
7) Washed with DMF (6 times for 20 sec. each)

After step 7, an aliquot was taken for a ninhydrin test. If the test was negative, one goes back to step 1 for coupling of the next amino acid. If the test was positive or slightly positive, steps 6 and 7 should be repeated.

The above scheme may be used for coupling each of the amino acids of the peptides described in this invention. Nα-protection with FMOC may also be used with each of the remaining amino acids throughout the synthesis.

Radiolabeled peptides may be prepared by incorporation of a tritiated amino acid using the above coupling protocol.

After the addition of the last amino acid, the Nα-FMOC of the N-terminal residue is removed by going back to steps 1-7 of the above scheme. The peptide resin is washed with $CH_2Cl_2$ and dried in vacuo to give the crude protected peptide.

PROCEDURE 3

Deprotection and Cleavage of the Peptides from the Resin

The protected peptide-resin was suspended in a 55% solution of trifluoroacetic acid (TFA) in $CH_2Cl_2$, containing 2.5% ethanedithiol and 2.5% anisole. The mixture was flushed with $N_2$ and stirred for 1.5 hours at room temperature. The mixture was filtered and the resin washed with $CH_2Cl_2$. The resin was treated again with 20% TFA in $CH_2Cl_2$ for 5 minutes at room temperature. The mixture was filtered and the resin washed with 20% TFA in $CH_2Cl_2$ and then washed with $CH_2Cl_2$. The combined filtrates were evaporated in vacuo below 35° C. and the residue triturated several times with dry dimethyl ether. The solid was dissolved in aqueous acetic acid and lyophilized to afford the crude product.

The peptides containing arg and cys residues are further deprotected by HF treatment at 0° C. for 1 hour in the presence of anisole and dimethylsulfide. The peptides were extracted with 10% aqueous acetic acid, washed with dimethyl ether and lyophilized to afford the crude peptides.

PROCEDURE 4

Purification of Peptides

The crude peptides were purified by preparative HPLC on a Vydac column (2.5×25 mm) of $C_{18}$ or $C_4$ reverse phase with a gradient of the mobile phase. The effluent was monitored at 220 nm and subsequently by analytical HPLC. Relevant fractions were pooled, evaporated and lyophilized. The identity of the synthetic peptides was verified by analytical reverse phase chromatography and by amino acid analysis.

PROCEDURE 5

Cyclization of Peptides

A solution of potassium ferricyanide (0.01M, pH 7.0) was added slowly to a dilute aqueous solution (0.5 mM) of the linear peptide at pH 7.0. After 24 hours at room temperature, the pH was lowered to 5.0 and the solution treated with ion exchange resin (Bio-Rad Ag-3-X4a, Cl-form) for 30 minutes. The suspension was filtered and the filtrate lyophilized to give the crude cyclic peptide. The peptide was purified by preparative reverse phase HPLC and characterized by amino acid analysis. Proof of cyclicity was obtained by comparing the HPLC mobility of the cyclic peptide with the starting linear peptide by reducing an aliquot of the cyclic peptide back to the linear peptide and also by observing the disappearance of free sulfhydryl groups (Ellman's Test) after the cyclization.

PROCEDURE 6

Conjugation of Peptides to Bovine Serum Albumin or Keyhole Limpet Hemocyanin

Peptides were conjugated to BSA or KLH previously derivatized with either sulfosuccinimidyl 4-(p-maleimidophenyl) butyrate (Sulfo-SMPB) or sulfosuccinimidyl 4-(N-maleimidomethyl) cyclohexane-1-carboxylate (Sulfo-SMCC).

An aqueous solution of sulfo-SMPB or sulfo-SMCC (Pierce Chemicals) was added to a solution of BSA or KLH in 0.02M sodium phosphate buffer (pH 7.0). The mixture was shaken at room temperature for 45 minutes and the activated carrier immediately applied to a Sephadex G-25 column equilibrated with 0.1M sodium phosphate buffer (pH 6.0) at 4° C.

The fractions of the first peak absorbance (280 nm) corresponding to activated carrier were combined in a round bottom flask to which was added a solution of peptide in 0.05 M sodium phosphate buffer (pH 6.2). The mixture was thoroughly flushed with $N_2$ and incubated overnight at room temperature. The coupling efficiency was monitored using $^3H$-labeled peptide and by amino acid analysis of the conjugate.

PROCEDURE 7

Detection of Antibodies to Rubella Virus by an Enzyme Linked Immunosorbent Assay (ELISA)

Each well of the microtiter plate was saturated with 100 μl of a solution containing a peptide or mixture of peptides (5 μg/ml) and left overnight. The wells were emptied and washed twice with a washing buffer (Tris, 0.043M; NaCl, 0.5M; thimerosal, 0.01% w/v; Tween 20, 0.05% v/v; pH 7.4). The wells were then saturated with 0.35 ml of washing buffer for 1 hour at 37° C. and washed once with the same buffer. Serum samples to be analyzed were diluted with specimen buffer (washing buffer plus casein, 0.05% w/v). The wells were rinsed with washing buffer prior to the addition of the diluted serum sample (0.1 ml). These were left to incubate for 1 hour at room temperature. The wells were then emptied, washed twice rapidly and then once for two minutes with washing buffer. The conjugate solution (peroxidase labeled affinity purified goat antibody to human IgG or to human IgM, 0.5 mg in 5 ml 50% glycerol) diluted with 1% w/v bovine serum albumin in washing buffer was added to each well (0.1 ml) and incubated for 1 hour at room temperature. The wells were then emptied and washed five times with the washing buffer. The substrate solution (3,3', 5,5'-tetramethylbenzidine, 8 mg per ml of DMSO) was diluted with 100 volumes 0.1M citrate-acetate buffer (pH 5.6) containing 0.1% v/v of 30% $H_2O_2$ and added to each well (0.1 ml per well). After 10 minutes, the contents of each well were treated with 0.1 ml 2N $H_2SO_4$ and the optical density read at 450 nm. All determinations were done in duplicate.

Using general procedures substantially as described above the following specific peptides were prepared; BCH-139, BCH-139 cyclic, BCH-140, BCH-140 cyclic, BCH-174, BCH-176, BCH-177, BCH-178, BCH-178 cyclic and BCH-229.

These peptides were then evaluated for their ability to detect Rubella-specific antibodies.

EXPERIMENT 1

In Experiment 1 peptides BCH-139, BCH-139 cyclic, BCH-140, BCH-140 cyclic, BCH-178 and BCH-178 cyclic were compared in ELISA assays using a panel of seropositive and seronegative serum and plasma samples obtained from a variety of Canadian, U.S. and European sources.

The results are displayed in Table 1.

TABLE 1

| | | O.D. MED ON PLATES WITH PETIDE (BCH-) | | | | | |
|---|---|---|---|---|---|---|---|
| SERUM NO. | HAI TITER | 139 | 139 cyc | 140 | 140 cyc | 178 | 178 cyc |
| (NEG. CONTROL) | | 0.014 | 0.016 | 0.025 | 0.010 | 0.025 | 0.015 |
| 1 | 256 | 0.143 | 0.150 | 1.482 | 1.689 | 1.669 | 1.911 |
| 2 | 0 | 0.125 | 0.115 | 0.110 | 0.050 | 0.246 | 0.135 |
| 3 | 0 | 0.071 | 0.064 | 0.117 | 0.200 | 0.135 | 0.102 |
| 4 | 128 | 0.140 | 0.130 | 0.246 | 0.250 | 1.420 | 1.674 |
| 5 | 0 | 0.420 | 0.441 | 0.205 | 0.140 | 0.202 | 0.203 |
| 6 | 1024 | 0.252 | 0.567 | 1.170 | 1.750 | 1.490 | 1.843 |
| 7 | 0 | 0.153 | 0.202 | 0.198 | 0.250 | 0.166 | 0.143 |
| 8 | 256 | 0.086 | 0.106 | 0.949 | 0.850 | 1.388 | 1.576 |
| 9 | 0 | 0.142 | 0.142 | 0.164 | 0.240 | 0.183 | 0.149 |
| 10 | 0 | 0.146 | 0.139 | 0.189 | 0.200 | 0.202 | 0.150 |
| 11 | 0 | 0.122 | 0.160 | 0.156 | 0.120 | 0.211 | 0.198 |
| cut off*: | | 0.214 | 0.216 | 0.225 | 0.210 | 0.225 | 0.215 |

*In this experiment, the cut off above which a sample is considered positive for the presence of rubella antibodies was defined as being equal to the O.D. value obtained with the negative control sample (sample dilution buffer) plus 0.200.

These results demonstrate that the cyclic peptides have higher sensitivity and specificity than the corresponding linear peptides. On average, the results using the cyclic peptides are higher when the serum is seropositive and lower when the serum is seronegative. These results also demonstrate the surprising superiority of BCH-178 cyclic as compared to even the other cyclic peptides.

EXPERIMENT 2

In Experiment 2 synthetic peptide BCH-178 cyclic is employed in an assay of Rubella-specific antibodies. The results are displayed in Table 2.

TABLE 2

| SERUM I.D.* | HAI | ELISA IgG** | ELISA IgM*** |
|---|---|---|---|
| A-1-1 | 256 | 2.622+ | 2.346+ |
| A-2-1 | 1024 | 2.850+ | 1.945+ |
| A-1-2 | 0 | 0.591+ | 0.047- |
| A-2-2 | 128 | 2.850+ | 0.537+ |
| A-1-3 | 0 | 0.304+ | 0.740+ |
| A-2-3 | 512 | 2.850+ | 2.626+ |
| A-1-4 | 0 | 0.157- | 0.219+ |
| A-2-4 | 2048 | 2.634+ | 1.087+ |
| A-1-5 | 0 | 0.252+ | 0.576+ |
| A-2-5 | 1024 | 2.850+ | 1.995+ |
| A-1-6 | 0 | -0.020- | -0.025- |
| A-2-6 | 256 | 2.368+ | 1.448+ |
| A-1-7 | 512 | 2.850+ | 1.772+ |
| A-1-8 | 1024 | 2.468+ | 2.000+ |
| A-1-9 | 512 | 2.637+ | 0.218+ |
| A-1-10 | 256 | 2.850+ | 0.448+ |
| A-1-11 | 256 | 1.925+ | 0.809+ |
| A-1-12 | 0 | 0.018- | 0.190+ |
| A-2-12 | 1024 | 2.850+ | 0.705+ |
| A-1-13 | 0 | 0.049+ | 0.626+ |
| A-2-13 | 512 | 2.850+ | 1.264+ |
| A-1-14 | 0 | 0.028- | 0.109- |
| A-2-14 | 256 | 2.392+ | 1.866+ |
| A-1-15 | 0 | 0.349+ | 1.206+ |
| A-2-15 | 256 | 2.343+ | 0.192- |
| A-1-16 | 0 | 0.020- | 0.316+ |
| A-2-16 | 1024 | 2.518+ | 0.230+ |
| A-1-17 | 0 | 0.096- | 0.337+ |
| A-2-17 | 512 | 2.516+ | 1.575+ |
| A-1-18 | 256 | 1.751+ | 2.800+ |
| A-1-19 | 512 | 2.285+ | 1.296+ |
| A-2-20 | 256 | 2.034+ | 0.722+ |
| A-1-21 | 64 | 1.254+ | 0.722+ |
| A-2-21 | 512 | 2.850+ | 0.616+ |
| A-1-22 | 0 | -0.059- | 0.163- |
| A-2-22 | 256 | 2.707+ | 0.404+ |
| A-1-23 | 128 | 0.766+ | 1.523+ |
| A-1-24 | 0 | -0.025- | 0.124- |
| A-2-24 | 256 | 2.324+ | 1.463+ |
| A-1-25 | 0 | -0.013- | 0.093- |
| A-2-25 | 512 | 2.627+ | 1.546+ |
| A-1-26 | 16 | 0.068- | 0.675 |
| A-2-26 | 1024 | 2.515+ | 1.153+ |
| A-1-27 | 512 | 1.327+ | 0.956+ |
| A-2-27 | 512 | 2.745+ | 0.526+ |
| A-1-28 | 512 | 2.850+ | 1.521+ |
| A-1-29 | 16 | 0.365+ | 0.992+ |
| A-1-30 | 0 | -0.019- | -0.091- |
| A-2-30 | 1024 | 2.090+ | 0.470+ |
| A-1-31 | 0 | 0.070+ | -0.043- |
| A-2-31 | 1024 | 1.762+ | 0.357+ |
| A-1-32 | 0 | 0.025- | 0.455+ |
| A-2-32 | 256 | 1.870+ | 1.485+ |
| A-2-33 | 256 | 1.859+ | 0.603+ |
| A-1-34 | 128 | 2.609+ | 2.471+ |
| A-1-35 | 0 | 0.095- | 0.111- |
| A-2-35 | 512 | 1.943+ | 0.683+ |
| A-1-36 | 256 | 1.095+ | 2.800+ |
| A-1-37 | 4096 | 2.721+ | 0.081- |
| A-1-38 | 32 | 0.036- | 1.048+ |
| A-2-38 | 512 | 2.058+ | 0.128- |
| A-1-39 | 64 | 0.420+ | 1.313+ |
| A-2-39 | 2048 | 2.656+ | 1.506+ |
| A-2-40 | 16384 | 2.520+ | 1.343+ |
| A-1-41 | 512 | 2.850+ | 1.863+ |
| A-2-41 | 512 | 2.850+ | 0.467+ |
| A-1-42 | 0 | 0.102- | 0.120- |
| A-2-42 | 4096 | 2.659+ | 1.403+ |
| A-1-43 | 1024 | 2.362+ | 1.295+ |
| A-1-44 | 128 | 1.372+ | 2.216+ |
| A-1-45 | 0 | 0.072- | 0.234+ |
| A-2-45 | 512 | 2.668+ | 1.579+ |
| A-2-46 | 512 | 2.484+ | 1.597+ |
| A-2-47 | 128 | 2.069+ | 0.948+ |
| A-2-48 | 256 | 2.743+ | 0.401+ |
| A-1-49 | 0 | -0.010- | 0.291+ |
| A-2-49 | 512 | 2.045+ | 0.525+ |
| A-1-50 | 256 | 2.640+ | 0.773+ |
| A-2-50 | 256 | 2.322+ | 0.330+ |
| A-1-51 | 64 | 1.694+ | 1.401+ |
| A-2-51 | 256 | 2.442+ | 0.165- |
| A-1-52 | 0 | 0.134- | 0.220+ |
| A-2-52 | 256 | 2.283+ | 0.697+ |
| A-1-53 | 0 | 0.020- | 0.110- |
| A-2-53 | 256 | 2.128+ | 0.013- |
| A-1-54 | 0 | -0.009- | -0.001- |
| A-2-54 | 256 | 2.850+ | 0.313+ |
| A-1-55 | 512 | 1.457+ | 0.443+ |
| A-2-55 | 512 | 2.118+ | 0.040- |
| A-1-56 | 128 | 0.883+ | 1.155+ |
| A-2-56 | 512 | 2.461+ | 0.429+ |
| A-1-57 | 512 | 2.537+ | 0.801+ |
| A-2-57 | 512 | 2.426+ | 0.101- |
| A-1-58 | 0 | -0.029- | 0.482+ |
| A-2-58 | 128 | 2.001+ | 0.454+ |
| A-1-59 | 256 | 2.439+ | 2.800+ |
| A-2-59 | 64 | 2.307+ | 2.232+ |
| A-1-60 | 16 | 0.033- | 0.293+ |
| A-2-60 | 256 | 2.198+ | 0.240+ |
| A-1-61 | 0 | 0.674+ | 0.024+ |
| A-2-61 | 2048 | 2.589+ | 0.460+ |
| A-1-62 | 128 | 1.643+ | 1.300+ |
| A-2-62 | 2048 | 2.583+ | 0.460+ |
| A-1-63 | 16 | 0.363+ | 1.322+ |
| A-2-63 | 1024 | 2.850+ | 0.591+ |
| A-1-64 | 0 | 0.307+ | 0.071- |
| A-2-64 | 512 | 1.586+ | 0.220+ |
| A-1-65 | 0 | 0.015- | 0.237+ |
| A-2-65 | 128 | 2.365+ | 0.015- |

*All serum and plasma samples are labeled A-i-j. The label "j" corresponds to a given donor; the label "i" is either 1 or 2 which indicates that it is the first (1) and in some cases the second (2) blood donation taken from this donor.
**This column contains the O.D. values measured and a qualitative "+" or "−" sign to indicate that the corresponding OD value indicates that the sample is either positive or negative for the presence of IgG against the rubella virus.
***Same as above, but for the presence of IgM antibody against the rubella virus.

These results demonstrate the unexpected sensitivity and specificity of this antigen. All 81 of the HAI positive samples were detected. Sixteen other samples—negative by HAI—were shown to be positive using BCH-178 cyclic. These latter results were then confirmed by second bleedings—two to four weeks later—which were positive in both HAI and ELISA assays.

EXPERIMENT 3

In Experiment 3 synthetic peptide BCH-178 cyclic was compared to peptides BCH-139, BCH-176 and BCH-177 in detecting Rubella-specific antibodies. The results are displayed in Table 3.

TABLE 3

| | | O. D. READINGS* SYNTHETIC PEPTIDE USED IN THE ELISA | | | |
|---|---|---|---|---|---|
| SERUM I.D. | HAI TITER | BCH-139 | BCH-176 | BCH-177 | BCH-178 cyclic |
| NEGATIVE CONTROL | | 0.014 | 0.016 | 0.019 | 0.015 |
| A-1-4 | 0 | 0.146 | 0.135 | 0.188 | 0.150 |
| A-1-5 | 0 | 0.122 | 0.128 | 0.194 | 0.198 |
| A-1-8 | 1024 | 0.252 | 0.143 | 0.258 | 1.843 |
| A-1-13 | 0 | 0.071 | 0.061 | 0.184 | 0.102 |
| A-1-16 | 0 | 0.125 | 0.104 | 0.141 | 0.135 |
| A-1-17 | 0 | 0.142 | 0.182 | 1.398 | 0.149 |
| A-1-32 | 0 | 0.153 | 0.170 | 0.132 | 0.143 |
| A-2-15 | 256 | 0.143 | 0.148 | 0.189 | 1.911 |
| A-2-33 | 256 | 0.086 | 0.120 | 0.190 | 1.388 |

*Cut-off in this test was set at (NEGATIVE CONTROL + 0.200).

These results demonstrate that BCH-178 cyclic is more specific and more sensitive than the other peptides. BCH-139 and BCH-177 each detected only one of the three seropositive samples. BCH-176 detected none of them. BCH-178 cyclic, on the other hand, detected all seropositives with no false positives.

While we have herein before described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented herein before by way of example.

We claim:

1. A linear peptide having the formula a—X—b wherein:

X is a sequence of at least six amino acids taken as a block from the amino acid sequence of the E1 glycoprotein of a strain of rubella virus that corresponds to $AA_{213}$–$AA_{239}$ of the E1 glycoprotein of the Judith strain of rubella virus as set forth in FIG. 1, which block maintains the sequence and N terminus to C terminus direction of the native amino acid sequence and analogues thereof, said analogues resulting from conservative substitutions in or modifications to the native amino acid sequence block;

a is selected from the group consisting of:
  (i) an amino terminus;
  (ii) one to eight amino acids taken as a block from and maintaining the sequence and N terminus to C terminus direction of that portion of the native amino acid sequence of the E1 glycoprotein immediately N-terminal to X or conservative substitutions in or modifications thereto; and
  (iii) a substituent effective to facilitate coupling of the peptide to another moiety; and b is selected from the group consisting of:
  (i) a carboxy terminus;
  (ii) one to eight amino acids taken as a block from and maintaining the sequence and N terminus to C terminus direction of that portion of the native amino acid sequence of the E1 glycoprotein immediately C-terminal to X or conservative substitutions in or modifications thereto; and
  (iii) a substituent effective to facilitate coupling of the peptide to another moiety.

2. The peptide according to claim 1, wherein X is BCH-178.

* * * * *